United States Patent
Manzer

(10) Patent No.: US 6,673,946 B2
(45) Date of Patent: Jan. 6, 2004

(54) MANUFACTURE OF 3-METHYL-TETRAHYDROFURAN FROM 2-METHYL-GAMMA-BUTYROLACTONE

(75) Inventor: Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/191,314

(22) Filed: Jul. 9, 2002

(65) Prior Publication Data

US 2003/0065198 A1 Apr. 3, 2003

Related U.S. Application Data

(60) Provisional application No. 60/304,086, filed on Jul. 10, 2001.

(51) Int. Cl.[7] .............................................. C07D 307/06
(52) U.S. Cl. ..................................................... 549/508
(58) Field of Search ......................................... 549/508

(56) References Cited

U.S. PATENT DOCUMENTS 4,973,717 A * 11/1990 Williams .................... 549/508
5,990,324 A     11/1999 Takemoto et al.

FOREIGN PATENT DOCUMENTS

JP      219981      8/1994
JP      217768      8/1996

OTHER PUBLICATIONS

Chemical Abstracts, vol. 121:157510 (1994).*

* cited by examiner

*Primary Examiner*—Bernard Dentz

(57) ABSTRACT

Disclosed is a hydrogenation process for the preparation of 3-methyl-tetrahydrofuran from 2-methyl-gamma-butyrolactone. The above process enables the production of the objective highly pure 3-methyl-tetrahydrofuran free from alcohol in high efficiency and high conversion through a simple production step.

9 Claims, No Drawings

MANUFACTURE OF 3-METHYL-TETRAHYDROFURAN FROM 2-METHYL-GAMMA-BUTYROLACTONE

This application claims priority from Provisional Application No. 60/304,086 filed Jul. 10, 2001.

FIELD OF INVENTION

Described is a process, for preparing 3-methyl-tetrahydrofuran from 2-methyl-gamma-butyrolactone.

BACKGROUND OF THE INVENTION

Substituted tetrahydrofuran, like 3-methyl-tetrahydrofuran of the present invention, is in general useful in those areas in which tetrahydrofuran is useful. Examples include polymerization to obtain fibers, and uses as a solvent.

Poly (tetra methylene ether glycol) is obtained by polymerization of tetrahydrofuran. This polymer is used as chain segments in polyurethanes and polyesters. Polyurethanes based on poly (tetra methylene ether glycol) soft-segment have improved hydrolytic stability, abrasion resistance and elastomeric properties. Other benefits include strength, toughness, durability, low compression set property, and high water vapor permeability. The largest end-use area is in spandex fibers for apparel. The products containing poly (tetra methylene ether glycol) are used in wheels, high-speed rolls, automotive parts, bushings, specialty hose, cable sheathing and coating, pipeline liners, roof, and floor coatings. The 3-methyl-tetrahydrofuran monomer can be utilized as a comonomer for modifying poly(tetra methylene ether glycol) to yield better elastomeric properties.

In use of tetrahydrofuran as a solvent where lower volatility is desired, 3-methyl-tetrahydrofuran is advantageous because tetrahydrofuran boils at 66° C. whereas 3-methyl-tetrahydrofuran boils at 86° C.

The present invention describes a process to prepare 3-methyltetrahydrofuran from 2-methyl-γ-butyrolactone with novel catalyst systems, without any alcohol production or separation. By "2-methyl-gamma-butyrolactone" is meant the compound described by the formula below.

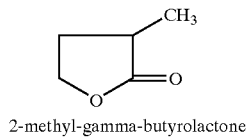

2-methyl-gamma-butyrolactone

Processes for producing 3-methyl-tetrahydrofuran by hydrogenation of an itaconic acid ester or a 3-formyl-2-methylpropionic acid ester, and by hydrogenation of a methyl-succinic ester are described in Japanese Patent Applications 219981/1994 and 217768/1996, respectively. Along with the objective 3-methyl-tetrahydrofuran, these reactions produce an alcohol, which has to be separated in a further step. The 3-methyl-tetrahydrofuran forms an azeotropic mixture with most of the lower alcohols, for example, with methanol having an azeotropic point at 64.5° C., and an azeotropic composition consisting of 25% by weight of 3-methyl-tetrahydrofuran and 75% by weight of methanol. The existence of this azeotrope necessitates a costly, energy intensive separation step to yield pure 3-methyl-tetrahydrofuran. In particular, the 3-methyl-tetrahydrofuran that is employed for modifying poly(tetramethylene glycol) can tolerate an alcohol impurity of not greater than 0.2%.

Similarly, U.S. Pat. No. 5,990,324 describes a three-step process for producing 3-methyl-tetrahydrofuran by hydrogenation of beta-formylisobutyric acid ester with the following general formula ROOC—CH(CH$_3$)—CH$_2$—CHO wherein, R is an alkyl group having 1 to 3 carbon atoms and the formyl group may be present as an acetal having an alkanol with 1 to 8 carbon atoms. In this process, the alcohol byproduct is separated from 2-methyl-gamma-butyrolactone in the second step. This separation can be effected by simple distillation. Although azeotropic distillation is not required, a separation of the alcohol is still a necessary step in the process of producing 3-methyl-tetrahydrofuran.

Thus, the problem to be solved is to provide a simple, economical, one-step process for the production of 3-methyl-tetrahydrofuran. The one-step process of the present invention describes a more efficient route a to produce 3-methyl-tetrahydrofuran from 2-methyl-gamma-butyrolactone with novel catalyst systems, without any alcohol production and therefore eliminating the step of azeotropic or other type of separation.

SUMMARY OF INVENTION

This invention relates to a process for producing 3-methyl-tetrahydrofuran (II), by hydrogenating 2-methyl-gamma-butyrolactone (I).

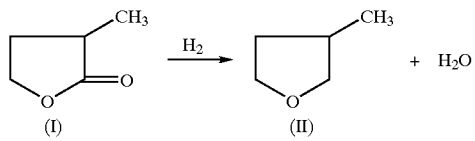

DETAILED DESCRIPTION OF THE INVENTION

This invention relates to synthesis of 3-methyl-tetrahydrofuran from 2-methyl-gamma-butyrolactone reactant. More specifically, this invention relates to synthesis of 3-methyl-tetrahydrofuran from 2-methyl-gamma-butyrolactone, which is free from an alcohol as a side product. The final product does not need separation or purification of alcohol. Unconverted 2-methyl-gamma-butyrolactone can be isolated and recycled to the hydrogenation reactor to increase the overall yield of the 3-methyl-tetrahydrofuran, the final product. Since 2-methyl-gamma-butyrolactone is a higher boiling substance, it can be condensed back to supplement the feed.

In the process herein, 2-methyl-gamma-butyrolactone is heated at temperatures set forth below, in the presence of hydrogen and thus reduced by hydrogenation to yield 3-methyl-tetrahydrofuran, the desired product. A metal catalyst, with or without a support may be present to effect the reduction reaction. An acid system may be used as a promoter to effect the reaction. A metal may also be optionally used as a promoter to aid the reaction.

The process of the present invention may be carried out in batch, or continuous mode in any of the equipment customarily employed for a continuous process. The water of the reaction is optionally removed from the reaction mass with the aid of an inert gas purge.

The temperature of the process is controlled in order to obtain a high yield of 3-methyl-tetrahydrofuran. The temperature of the reaction can range of from about 100° C. to about 250° C. A temperature of from about 200° C. to about 250° C. is preferred. A more preferred temperature is from about 215° C. to about 240° C. A pressure of from about 1

MPa to about 15 MPa is employed in the reaction. A pressure of from about 8 MPa to about 10 MPa is preferred.

By "acid promoter" is meant a compound acidic in nature that is added to enhance the physical or chemical function of a catalyst.

By "metal promoter" is meant a metallic compound that is added to enhance the physical or chemical function of a catalyst.

A catalyst is a substance that affects the rate of the reaction but not the reaction equilibrium, and emerges from the process, chemically unchanged. A chemical promoter generally augments the activity of a catalyst. The promoter may be incorporated into the catalyst during any step in the chemical processing of the catalyst constituent. The chemical promoter generally enhances physical or chemical function of the catalyst agent, but it can also be added to retard undesirable side reactions.

Reduction of 2-methyl-gamma butyrolactone to 3-methyl-tetrahydrofuran product and water is effected in presence of a metal catalyst. The catalytic metal component of the catalyst is selected from the group consisting of metals of Group 7, 8, 9, and 10, of the Periodic Table, compounds of a metal of group 7, 8, 9, and 10 of the Periodic Table, compounds thereof, combinations thereof, copper, and copper compounds.

The catalytic metal used in the process disclosed here may be used as a supported or as an unsupported catalyst. A supported catalyst is one in which the active catalyst agent is deposited on a support material by spraying, soaking or physical mixing, followed by drying, calcination, and if necessary, activation through methods such as reduction or oxidation. Materials frequently used as support are porous solids with high total surface areas (external and internal) which can provide high concentrations of active sites per unit weight of catalyst. The catalyst support may enhance the function of the catalyst agent. A catalyst which is not supported on a catalyst support material is an unsupported catalyst.

A support material is selected from the group consisting of carbon, alumina, silica, silica-alumina, titania, and a combination thereof. Moreover, supported catalytic metal/s may have the same supporting material or different supporting material. A more preferred support is carbon. The carbon can be a commercially available carbon such as Calsicat C, Sibunit C, or Calgon C (sold under the tradename Centaur (R)).

A preferred catalytic metal content range in a supported catalyst is from about 0.1% to about 25%. One preferred catalytic metal content is from about 1% to about 7%, and a further preferred catalytic metal content is from about 1% to about 5%. Another preferred catalytic metal content is from about 18% to about 22%.

Preferred combinations of catalytic metal and support system includes rhodium on carbon, rhenium on carbon, rhenium on alumina, iridium on carbon, iridium on alumina, ruthenium on alumina, and a combination of (ruthenium and rhenium) on carbon.

An acid promoter may be used in the process of the present invention. Suitable promoters include, those acids with a pKa less than about 4, preferably with a pKa less than about 2, including inorganic acids, organic sulfonic acids, heteropolyacids, perfluoroalkyl-sulfonic acids, and mixtures thereof. Also suitable are metal salts of acids with pKa less than about 4, including metal sulfonates, metal trifluoroacetates, metal triflates, and mixtures thereof including mixtures of salts with their conjugate acids. Specific examples of promoters include sulfuric acid, fluorosulfonic acid, phosphoric acid, p-toluenesulfonic acid, benzenesulfonic acid, phosphotungtstic acid, phosphomolybdic acid, trifluromethanesulfonic acid, 1,1,2,2-tetrafluroethanesulfonic acid, 1,2,3,2,3,3-hexapropanesulfonic acid, bismuth triflate, yttrium triflate, ytterbium triflate, neodymium triflate, lanthanum triflate, scandium triflate, and zirconium triflate. A preferred promoter is selected from group consisting of $Zn(BF4)_2$, zeolite CBV-1502, zeolite 20A, zeolite CBV 3020E, 13% Nafion(R) and methane sulfonic acid. The acid promoter is used in concentration of from 0.1% to 5% by weight of the reactant. A preferred concentration of the promoter is in the range of 0.25% to 2.5% by weight of the reactant.

Suitable heterogeneous acid promoters are zeolites, fluorinated alumina, acid-treated silica, acid treated silica-alumina, acid treated clays, heterogeneous heteropolyacids and sulfated zirconia. Heterogeneous acid promoters are preferred due to ease of separation, but both heterogeneous and homogeneous acid promoters may be used.

A metal promoter may be used optionally with the acid promoter in the process of the present invention. Suitable metal promoters include tin, zinc, copper, gold, silver, and combinations thereof. The preferred metal promoter is tin.

Experimental

The following abbreviations are used in the Examples:

| | |
|---|---|
| ESCAT | Series of catalysts provided by Engelhard Corp. |
| Calsicat Carbon | Catalyst support from Engelhard Corp. |
| Sibunit Carbon | Catalyst support from Inst. of Technical Carbon, Omsk, Russia |
| JM-A11108 Carbon | Catalyst support from Johnson Matthey, Inc. |
| Calgon Carbon | Catalyst support from Calgon Corp. under the brand name of Centaur(R) |
| CBV-3020E | Type of Zeolite acid promoter |
| 20-A | Type of Zeolite acid promoter |
| CBV-1502 | Type of Zeolite acid promoter |

A commercially available support such as carbon, alumina, silica, silica-alumina, titania available from Engelhard Corp. (E. Windsor, Conn.) was impregnated by incipient wetness with a metal salt. The precursors used were $NiCl_2.6H_2O$ (Alfa Chemical Co.), $Re_2O_7$ (Alfa Chemical Co.), $PdCl_2$ (Alfa Chemical Co.), $RuCl_3.xH_2O$ (Aldrich Chemical Co.). $H_2PtCl_6$ (Johnson Matthey, Inc., W. Deptford, N.J.), $CrCl_3.6H_2O$ (Mallinckrodt Baker, Inc.), 5% Rh using $RhCl_3.xH_2O$ (Alfa Chemical Co.). The samples were dried and reduced at 300–450° C. in $H_2$ for 2 hours.

The carbon used was commercially available as Calsicat Carbon, Sibunit Carbon, or Calgon Carbon (Centaur(R)). Calsicat Carbon is lot. no. S-96-140 from Engelhard Corp, Beachwood, Ohio. Sibunit Carbon is Sibunit-2 from Institute of Technical Carbon, 5th Kordnaya, Omsk 64418, Russia. Calgon Carbon is PCB Carbon from Calgon Corp. (under the registered trademark of Centaur(R)).

EXAMPLE-1

Catalyst Preparation

5%Pt on Acid Washed Calsicat Carbon

In a 150 ml beaker, a solution was made up of 4.5 ml, 0.3 M $H_2PtCl_6$ with 4.0 ml deionized $H_2O$. To the beaker were added 4.75 g Calsicat Acid Washed Carbon (12×20 mesh, dried at 120° C. overnight). The slurry was allowed to stand at room temperature for 1 hr with occasional stirring and then dried at 120° C. overnight with frequent stirring (until free flowing).

In an alumina boat, in a quartz lined tube furnace, the catalyst was purged with 500 SCCM N$_2$ at room temperature for 15 min and then with 100 SCCM He at room temperature for 15 min. The catalyst was heated to 150° C. and held at 150° C. under He for 1 hr. At this point, 100 SCCM H$_2$ were added and the sample was held at 150° C. under He and H$_2$ for 1 hr. The temperature was increased to 300° C. and the catalyst was reduced at 300° C. under He—H$_2$ for 8 hrs. The H$_2$ was stopped, the sample was held at 300° C. under He for 30 min and then cooled to room temperature in flowing He. The catalyst was finally passivated in 1.5% O$_2$ in N$_2$ at 500 SCCM for 1 hour at room temperature and weighed 4.93 grams when unloaded.

EXAMPLES 1–64
Reduction of 2-methyl-gamma-butyrolactone to 3-methyl-tetrahydrofuran 50% 2-methyl-gamma-butyrolactone in dioxane (970.0 mg, 4.84 mmole) and an amount of catalyst and support as indicated in Table 1, were added to a 2 ml reactor. The reactor was sealed and charged with 6.89 MPa of H$_2$, and heated to 225° C. then cooled rapidly. The reaction was stopped after 4 hours. An internal standard (2-methoxy ethyl ether) was added to the reaction mixture and GC analysis was performed on a HP-6890 GC with a Chrompack column (CP-WAX 58, 25 M×0.25 MM). An acid promoter was not used for examples 1–33. An acid promoter was used for examples 34–66.

TABLE 1

| Ex. No. | Time (hrs) | Temp. (° C.) | H$_2$ Pressure (MPa) | Catalyst/Support | Acid | 2-Me-GBL Conversion (%) | 3-methyl-tetrahydrofuran Selectivity (%) |
|---|---|---|---|---|---|---|---|
| 1. | 4 | 225 | 6.89 | 1% Ru/6% Re/C | | 19.56 | 49.12 |
| 2. | 4 | 225 | 6.89 | 5% Rh/Sibunit C | | 9.21 | 12.76 |
| 3. | 4 | 225 | 6.89 | 5% Pt/Sibunit C | | 2.12 | 29.23 |
| 4. | 4 | 225 | 6.89 | 5% Ru/Calsicat C | | 9.87 | 77.56 |
| 5. | 4 | 225 | 6.89 | 5% Rh/Calsicat C | | 5.12 | 91.38 |
| 6. | 4 | 225 | 6.89 | 5% Pd/Calsicat C | | 2.44 | 70.21 |
| 7. | 4 | 225 | 6.89 | 5% Re/Calsicat C | | 31.24 | 97.91 |
| 8. | 4 | 225 | 6.89 | 5% Ir/Calsicat C | | 8.95 | 92.01 |
| 9. | 4 | 225 | 6.89 | 5% Pt/Sibunit C | | 2.40 | 82.19 |
| 10. | 4 | 225 | 6.89 | 5% Ru/Al$_2$O$_3$ | | 1.60 | 95.57 |
| 11. | 4 | 225 | 6.89 | 5% Rh/Al$_2$O$_3$ | | 26.60 | 3.45 |
| 12. | 4 | 225 | 6.89 | 5% Pd/Al$_2$O$_3$ | | 88.01 | 0.80 |
| 13. | 4 | 225 | 6.89 | 5% Re/Al$_2$O$_3$ | | 7.33 | 97.75 |
| 14. | 4 | 225 | 6.89 | 5% Ir/Al$_2$O$_3$ | | 2.00 | 96.21 |
| 15. | 4 | 225 | 6.89 | 5% Pt/Al$_2$O$_3$ | | 10.62 | 24.69 |
| 16. | 4 | 225 | 6.89 | 5% Ru/SiO$_2$ | | 5.50 | 10.01 |
| 17. | 4 | 225 | 6.89 | 5% Rh/SiO$_2$ | | 19.51 | 1.67 |
| 18. | 4 | 225 | 6.89 | 5% Pd/SiO$_2$ | | 31.30 | 1.23 |
| 19. | 4 | 225 | 6.89 | 5% Re/SiO$_2$ | | 8.46 | 41.56 |
| 20. | 4 | 225 | 6.89 | 5% Ir/SiO$_2$ | | 1.83 | 31.17 |
| 21. | 4 | 225 | 6.89 | 5% Pt/SiO$_2$ | | 17.41 | 3.50 |
| 22. | 4 | 225 | 6.89 | 5% Re/Sibunit C | | 32.87 | 53.09 |
| 23. | 4 | 225 | 6.89 | 5% Re/Calgon C | | 14.50 | 31.75 |
| 24. | 4 | 225 | 6.89 | 5% Re/Sibunit C(400C) | | 42.45 | 31.39 |
| 25. | 4 | 225 | 6.89 | 5% Re/Sibunit C(450C) | | 24.33 | 46.33 |
| 26. | 4 | 225 | 6.89 | 10% Re/Sibunit C(400C) | | 36.34 | 35.26 |
| 27. | 4 | 225 | 6.89 | 10% Re/Sibunit C(450C) | | 44.95 | 30.02 |
| 28. | 4 | 225 | 6.89 | 5% Re/Calsicat C(400C) | | 36.24 | 94.20 |
| 29. | 4 | 225 | 6.89 | 5% Re/Calsicat C(450C) | | 35.77 | 91.63 |
| 30. | 4 | 225 | 6.89 | 10% Re/Calsicat C(400C) | | 46.13 | 90.11 |
| 31. | 4 | 225 | 6.89 | 10% Re/Calsicat C(450C) | | 49.41 | 91.19 |
| 32. | 4 | 225 | 6.89 | 20% Re/Calsicat C(400C) | | 64.74 | 86.26 |
| 33. | 4 | 225 | 6.89 | 20% Re/Calsicat C(450C) | | 72.11 | 78.25 |
| 34. | 4 | 225 | 6.89 | 1% Ru/6% Re/C | Zn(BF4)2 | 18.68 | 80.61 |
| 35. | 4 | 225 | 6.89 | 1% Ru/6% Re/C | CBV-1502 | 10.94 | 89.96 |
| 36. | 4 | 225 | 6.89 | 1% Ru/6% Re/C | 20A | 2.70 | 48.33 |
| 37. | 4 | 225 | 6.89 | 5% Rh/Sibunit C | Zn(BF4)2 | 6.15 | 6.79 |
| 38. | 4 | 225 | 6.89 | 5% Rh/Sibunit C | CBV-1502 | 2.21 | 40.48 |
| 39. | 4 | 225 | 6.89 | 5% Pt/Sibunit C | Zn(BF4)2 | 1.37 | 31.66 |
| 40. | 4 | 225 | 6.89 | 5% Pt/Sibunit C | CBV-1502 | 4.83 | 6.35 |
| 41. | 4 | 225 | 6.89 | 5% Pd/Calsicat C | Zn(BF4)2 | 10.08 | 92.06 |
| 42. | 4 | 225 | 6.89 | 5% Pd/Calsicat C | CBV-3020E | 4.75 | 8.31 |
| 43. | 4 | 225 | 6.89 | 5% Pd/Calsicat C | 13% NAFION | 1.37 | 18.57 |
| 44. | 4 | 225 | 6.89 | 5% Pd/Calsicat C | MSA | 2.48 | 11.71 |

TABLE 1-continued

| Ex. No. | Time (hrs) | Temp. (° C.) | H₂ Pressure (MPa) | Catalyst/ Support | Acid | 2-Me-GBL Conversion (%) | 3-methyl-tetrahydrofuran Selectivity (%) |
|---|---|---|---|---|---|---|---|
| 45. | 4 | 225 | 6.89 | 5% Ru/Calsicat C | Zn(BF4)2 | 6.90 | 86.35 |
| 46. | 4 | 225 | 6.89 | 5% Ru/Calsicat C | CBV-3020E | 3.16 | 62.88 |
| 47. | 4 | 225 | 6.89 | 5% Ru/Calsicat C | 13% NAFION | 6.11 | 57.65 |
| 48. | 4 | 225 | 6.89 | 5% Ru/Calsicat C | MSA | 8.59 | 32.53 |
| 49. | 4 | 225 | 6.89 | 5% Re/Calsicat C | Zn(BF4)2 | 4.07 | 72.97 |
| 50. | 4 | 225 | 6.89 | 5% Re/Calsicat C | CBV-3020E | 8.42 | 79.78 |
| 51. | 4 | 225 | 6.89 | 5% Re/Calsicat C | 13% NAFION | 10.21 | 91.35 |
| 52. | 4 | 225 | 6.89 | 5% Re/Calsicat C | MSA | 16.03 | 92.79 |
| 53. | 4 | 225 | 6.89 | 5% Rh/Calsicat C | Zn(BF4)2 | 0.69 | 57.72 |
| 54. | 4 | 225 | 6.89 | 5% Rh/Calsicat C | CBV-3020E | 1.01 | 70.50 |
| 55. | 4 | 225 | 6.89 | 5% Rh/Calsicat C | 13% NAFION(R) | 1.14 | 42.94 |
| 56. | 4 | 225 | 6.89 | 5% Rh/Calsicat C | MSA | 2.34 | 38.14 |
| 57. | 4 | 225 | 6.89 | 5% Pt/Sibunit C | Zn(BF4)2 | 2.01 | 35.66 |
| 58. | 4 | 225 | 6.89 | 5% Pt/Sibunit C | CBV-3020E | 0.61 | 31.75 |
| 59. | 4 | 225 | 6.89 | 5% Pt/Sibunit C | 13% NAFION | 2.07 | 30.65 |
| 60. | 4 | 225 | 6.89 | 5% Pt/Sibunit C | MSA | 2.67 | 24.09 |
| 61. | 4 | 225 | 6.89 | 5% Ir/Calsicat C | Zn(BF4)2 | 1.39 | 71.80 |
| 62. | 4 | 225 | 6.89 | 5% Ir/Calsicat C | CBV-3020E | 2.63 | 54.40 |
| 63. | 4 | 225 | 6.89 | 5% Ir/Calsicat C | 13% NAFION(R) | 1.77 | 63.55 |
| 64. | 4 | 225 | 6.89 | 5% Ir/Calsicat C | MSA | 3.03 | 55.50 |

What is claimed is:

1. A process for preparing 3-methyl-tetrahydrofuran comprising heating 2-methyl-gamma-butyrolactone represented by formula (I) in the presence of hydrogen a catalytic amount of a metal catalyst and a catalyst promoter

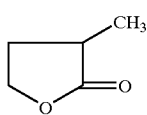
(I)

wherein said catalyst is selected from a group consisting of copper, cobalt, nickel, iron, rhenium, palladium, ruthenium, platinum, rhodium, manganese, iridium, technetium, osmium, gold, compounds thereof, and combinations thereof;

wherein, said catalyst promoter is selected from group consisting of tin, zinc, copper, gold, silver, sulfuric acid, fluorosulfonic acid, phosphoric acid, p-toluenesulfonic acid, benzenesulfonic acid, phosphotungtstic acid, phosphomolybdic acid, trifluromethanesulfonic acid, 1,1,2,2-tetrafluorethanesulfonic acid, 1,1,1,2,3,4-hexafluorpropanesulfonic acid, bismuth triflate, yttrium triflate, ytterbium triflate, neodymium triflate, lanthanum triflate, scandium triflate, zirconium triflate, heteropolyacids supported on zirconia, titania, $Zn(BF_4)_2$, methane sulfonic acid, Nafion®;

wherein said catalyst is supported on a catalyst support and wherein said catalyst support is selected from group consisting of carbon, alumina, silica, zirconia, silica-alumina, titania, compounds thereof and combinations thereof;

wherein said process is performed at a temperature from about 100° C. to about 250° C;

wherein said process is performed at a pressure from about 1.0 MPa to about 15.0 MPa;

with a proviso that said catalyst is not a combination of a rhenium catalyst in combination with group VIII elements of the Periodic Table and an acidic substance, and with a proviso that said catalyst is not a rhenium catalyst supported on carbon.

2. The process as recited in claim 1, wherein said process is performed at a temperature from about 200° C. to about 250° C.

3. The process as recited in claim 2, wherein said process is performed at a temperature from about 215° C. to about 240° C.

4. The process as recited in claim 1, wherein the process is performed at a pressure from about 1.0 MPa to about 15.0 MPa.

5. The process as recited in claim 4, wherein said process is performed at a pressure from about 8.0 MPa to about 10.0 MPa.

6. The process as recited in claim 1, wherein the process is performed at a temperature from about 215° C. to about 250° C. and a pressure from about 8.0 MPa to about 10.0 MPa.

7. The process as recited in claim 6, wherein the metal catalyst is present in an amount from 0.1% to 5.0%.

8. The process as recited in claim 6, wherein the metal catalyst is present in an amount from 5.0% to 10.0%.

9. The process as recited in claim 6, wherein the metal catalyst is present in an amount from 10.0 to 20.0%.

* * * * *